United States Patent [19]

Hasegawa

[11] 4,376,095

[45] Mar. 8, 1983

[54] HOLLOW FIBER-TYPE ARTIFICIAL LUNG HAVING ENCLOSED HEAT EXCHANGER

[75] Inventor: Hiroshi Hasegawa, Hiratsuka, Japan

[73] Assignee: Terumo Corporation, Tokyo, Japan

[21] Appl. No.: 292,941

[22] Filed: Aug. 14, 1981

[30] Foreign Application Priority Data

Aug. 25, 1980 [JP] Japan ................................ 55-115868

[51] Int. Cl.[3] ................................................ A61M 1/03

[52] U.S. Cl. ................................ 422/46; 128/DIG. 3; 261/DIG. 28; 422/48

[58] Field of Search .................................... 422/46, 48; 261/DIG. 28; 128/DIG. 3

[56] References Cited

U.S. PATENT DOCUMENTS 3,807,958 4/1974 Brumfield et al. .
3,856,475 12/1974 Marx ..................................... 422/46
3,998,593 12/1976 Yoshida et al. ........................ 422/46
4,138,288 2/1979 Lewin .
4,239,729 12/1980 Hasegawa et al. ................... 422/48
4,268,279 5/1981 Shindo et al. ..................... 422/48 X
4,306,018 12/1981 Kirkpatrick ...................... 422/46 X

FOREIGN PATENT DOCUMENTS 2617208 7/1977 Fed. Rep. of Germany ........ 422/46
55-2982 1/1980 Japan .

*Primary Examiner*—Barry S. Richman
*Attorney, Agent, or Firm*—Frishauf, Holtz, Goodman & Woodward

[57] ABSTRACT

A hollow fiber-type artificial lung having an enclosed heat exchanger comprises a first housing and a second housing connected together coaxially. A gas exchange chamber is defined in the first housing by a pair of spaced walls and a bundle of hollow fibers designed for gas exchange arranged in the first housing and between the pair of walls. The hollow fiber bundle is preferably constricted at the central portion to increase the packing ratio of the hollow fibers. The second housing is connected to the first housing by way of a blood chamber and has a pair of spaced apart walls, and multiple tubes which extend lengthwise between the pair of walls to effect heat exchange between a circulating heat exchange medium and the blood flowing through the multiple tubes.

9 Claims, 4 Drawing Figures

A
B
1
2
3
4
5
8
9
10
11
12
13
14
15
16
21
22'
24
25
26
27
28
29
30
31
32
33
34
35
36
37
38
41
51
52
54

HOLLOW FIBER-TYPE ARTIFICIAL LUNG HAVING ENCLOSED HEAT EXCHANGER

BACKGROUND OF THE INVENTION

1. Field of the Invention

This invention relates to a hollow fiber-type artificial lung having an enclosed heat exchanger.

2. Description of the Prior Art

In general, when a patient's blood is conducted extra-corporeally for oxygenation, as in the case of heart surgery, an artificial lung is used in the extra-corporeal circulating circuit. If the patient's blood is circulated through the circuit at ambient or lower temperatures, the blood is cooled during extra-corporeal circulation and therefore must be warmed to the patient's body temperature when exiting from the circuit. For this purpose a heat exchanger is used in the extra-corporeal circulating circuit. The heat exchanger may also be used for cooling the blood when resorting to a low body temperature process.

The prior-art apparatus in which an oxygenator and a heat exchanger are assembled as one unit, is disclosed in U.S. Pat. Nos. 3,807,958 and 4,138,288. In these patents, oxygen is blown into blood for blood oxygenation. This necessitated a defoamer to suppress the resulting foaming of the blood, adding to the size of the overall artificial lung apparatus.

In addition, with the artificial lung disclosed in these patents, the blood guide channel from the blood inlet to the outlet is so complex that the blood flow may undergo excess turbulence with the resulting risk of hemolysis. Moreover, because of the complexity of the guide channel, blood priming may be increased and the defoaming operation during such priming may present major difficulties.

As a solution to this problem, Japanese Patent Publication No. 2982/1980 discloses a stacked membrane type artificial lung having an enclosed heat exchanger. However, the oxygenator section and the heat exchanger section are of the stacked membrane type and are difficult to manufacture. In addition, the membrane type artificial lung may give rise to liquid leakage during use and therefore is not preferred.

At the present time, the hollow fiber type artificial lung is considered to be the device best suited for use as an artificial lung. However, a hollow fiber type artificial lung that has an enclosed heat exchanger has not been known to date.

SUMMARY OF THE INVENTION

It is an object of the present invention to provide a hollow fiber type artificial lung that has an enclosed heat exchanger.

The hollow fiber type artificial lung having an enclosed heat exchanger according to this invention comprises an oxygenator section, said oxygenator section including a first housing, a bundle of a multiplicity of hollow fibers designed for gas exchange, said hollow fibers having a mean pore size of 200 to 2,000 angstroms and being gas permeable and liquid impermeable, said hollow fibers being physically separated from one another and arranged side by side within and along the longitudinal direction of said first housing, first and second walls liquid-tightly carrying said fibers at the end portion of said fibers, with said end portions of said fibers left open, and defining an oxygen chamber with the inner wall of said first housing and the outer wall surfaces of said hollow fibers, oxygen inlet and outlet means communicating with said oxygen chamber, and a first blood circulation opening communicating with an interstitial space of said hollow fibers externally of said first wall. The multiple tube type heat exchanger section, comprises a second housing, a multiplicity of tubes physically separated from one another and arranged side by side within and along the longitudinal direction of said second housing, third and fourth walls liquid-tightly carrying said tubes at the end portions of said tubes, with said end portions of said tubes left open, and defining a heat exchange medium chamber with the inner wall of said second housing and the outer wall surfaces of said tubes, heat exchange medium inlet and outlet means communicating with said heat exchange medium chamber, and a second blood circulation opening communicating with an interstitial space of said externally of said fourth wall. The oxygenator section and the heat exchanger section are connected together at said first and second housings by a flow buffering blood chamber between said second and third walls which communicate the ends of the hollow fibers with the ends of the heat exchange tubes in face-to-face fashion.

According to a preferred embodiment of the invention, the first and second housings have connection terminuses of the same diameter provided with external threads advancing in opposite directions, said first and second housings being connected by a threaded connector ring externally of said connection terminuses with a sealing member interposed between said terminuses.

According to another preferred embodiment of the invention, the first and second housings each have connection terminuses of different diameters, and may be connected together with a sealing member between said terminuses.

With the blood chamber serving as a buffer, the processing capability of said oxygenator section and that of said heat exchanger section may be determined independently of each other.

In general, the hollow fibers are made of a polyolefin. The polyolefin hollow fibers typically have a mean pore diameter of about 200 to 2000 angstroms and a porosity of about 20 to 80 percent. In measuring the mean pore diameter of the hollow fiber, the pores on the inner and outer surfaces of the sample are observed with a scanning type electron microscope, manufactured by Nippon Denshi KK, magnification factor about 10,000, along with standard particles (such as uniform latex particles manufactured by Dow Chemical Inc.) and the pore diameter is measured on the basis of the standard particle size. If the pores are circular, the mean value of the measured pore diameters is adopted as the mean pore diameter. If the pores are elliptical, the long and short axes of the ellipsis are measured, and the area S of the ellipsis is then measured by using the formula $S=\pi ab/4$ (where a and b stand for the long and short axes), the pore diameter is then calculated with the area of the ellipsis converted into that of a circle, and the mean value of the calculated pore diameters is adopted as the mean pore diameter.

According to a further preferred embodiment of the invention, the inner wall of the first housing is formed with a constrictor for constricting the hollow fiber bundle at a mid portion longitudinally of said hollow fiber bundle.

DESCRIPTION OF THE PREFERRED EMBODIMENT

Figure 1:
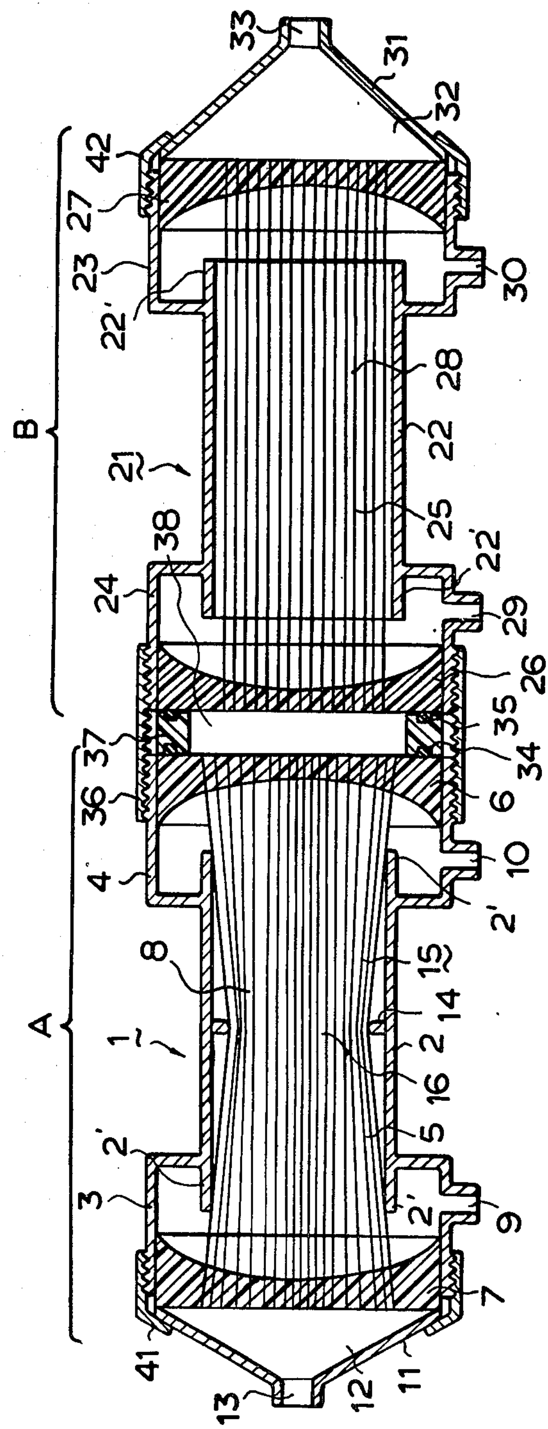
FIG. 1 is a sectional view of a hollow fiber type artificial lung having an enclosed heat exchanger according to a preferred embodiment of the present invention.

As shown in FIG. 1, the hollow fiber type artificial lung with an enclosed heat exchanger according to the present invention comprises a hollow fiber type oxygenator section A and a heat exchanger section B that are integrally connected to each other. The oxygenator section A has a housing 1 formed by a tubular main body 2 and threaded annular mounting covers 3, 4 secured to both ends of the main body 2. A multiplicity of, for example, 10,000 to 60,000 separate hollow fibers are arranged over the entire sectional area of and parallel to the longitudinal direction of the housing 1. The ends of these hollow fibers 5 are not plugged and are retained in liquid-tight manner by walls 6, 7 in the mounting covers 3, 4. The walls 6, 7 cooperate with the outer peripheral surface of the fibers 5 and the inner surface of the housing to define an enclosed oxygen chamber 8, at the same time isolating the chamber 8 from the blood circulating space, not shown, delimited within each of the hollow fibers 5.

The mounting cover 3 has an oxygen inlet 9 while the mounting cover 4 has an oxygen outlet 10.

The outer surface of the wall 7 is covered by a blood port 11, the inner surface of which delimits a blood influx chamber 12 with the outer surface of the wall 7. The blood port 11 has a blood inlet 13, and is secured to the mounting cover 3 by a threaded ring 41.

Preferably, a constrictor 14 is projectingly mounted axially and centrally of the inner surface of the tubular main member 2 of the housing 1. The constrictor 14 is formed on the inner surface of the tubular member 2 integrally with the tubular member 2 for constricting the outer periphery of the fiber bundle 15 consisting of a multiplicity of the hollow fibers 5 that are introduced into the tubular main member 2. Thus the bundle 15 is constricted axially centrally as shown in FIG. 1 for providing a constricted portion 16. Thus the packing ratio of the hollow fibers 5 (the ratio of an integrated sectional area of the fibers 5 to the sectional area of the bundle 15) differs with various axial portions of the bundle 15 and is highest at the central portion. For reasons stated below, the following values of the packing ratio are most desirable. First, the packing ratio at the central constricted portion 16 is about 60 to 80 percent, the packing ratio at other portions inside the tubular main body 2 is about 30 to 60 percent, and the packing ratio at both ends of the bundle 15, that is, on the outer surfaces of the walls 6, 7, is about 20 to 40 percent.

The hollow fibers 5 are made of porous polyolefin resin such as polypropylene or polyethylene, with polypropylene being preferred. In this case, the hollow fibers 5 have a multiplicity of small pores or holes interconnecting the inside and outside of the fiber wall. The hollow fiber has an inside diameter of about 100 to 1,000 μm, a wall thickness of about 10 to 50 μm and a porosity in the range of about 20 to 80 percent. With these polyolefin hollow fibers 5, membrane resistance to gas flow may be reduced and gas exchange performance may be enhanced markedly because the gas flow occurs as a volume flow.

Porous polypropylene or polyethlene as hollow fiber material should not be applied as it is to the oxygenator, but the surface of the material to make contact with the blood should be coated preferably with thrombus resisting material. For instance, polyalkylsulfon, ethyl cellulose or polydimethyl siloxane, or other materials having excellent gas permeability, may be applied to a thickness of about 1 to 20 μm. In this case, vaporization of water vapor contained in the blood may be prevented by having the membranous holes of the hollow fibers 5 coated to such a degree as will not effect the gas permeability of the hollow fibers. During operation of the oxygenator section, the pressure on the blood side is usually higher than the pressure on the oxygen side, but this relation may happen to be reversed for some reason, resulting in the danger that small air bubbles may flow into the blood. This risk may be prevented by having the membranous holes coated with thrombus resisting material, as discussed in the foregoing. Needless to say, such coating is effective to prevent blood coagulation or the formation of microsized blood clots.

Next, the preparation of walls 6, 7 will be described in detail. The walls 6, 7 serve the important purpose of isolating the inside and outside of the hollow fibers 5 from each other, as discussed in the foregoing. Usually, the walls 6, 7 are prepared by having a polymeric potting agent, such as polyurethane, silicone, epoxy resin etc., poured on to the inner wall surfaces on either end of the housing 1 by centrifugal injection and hardened in situ. More specifically, both opening ends of the multiple hollow fibers 5, longer than the length of the housing 1, are plugged with tightly viscous resin, and the fibers 5 are then placed side by side within the tubular main body 2 of the housing 1. Both ends of the hollow fibers 5 are covered completely with cover molds which are larger than the diameter of the mounting covers 3, 4. Then, the polymeric potting agent is poured from both ends while the housing 1 is kept rotating about its central axis. After the poured resin has hardened, the cover molds are removed and the outer end faces of the hardened resin are cut with a knife for exposing both open ends of the hollow fibers 5 to complete the preparation of the walls 6, 7.

In the above embodiment, because the hollow fiber bundle 15 is enlarged in diameter at both ends and reduced in diameter at the central portion by the constrictor 14, the packing ratio of the hollow fibers 5 is increased at the constricted central portion 16, and the fibers 5 are evenly distributed within the tubular main member 2. Therefore, the oxygen gas may be distributed more uniformly than in the case where the constriction 16 is not formed, resulting in a more stable gas flow and improved oxygen-carbon dioxide gas exchange efficiency. Moreover, since the inner sectional area of the housing 1 is changed abruptly at the central constriction 16, the oxygen gas flow rate is abruptly changed in this portion, resulting in an increased oxygen gas flow rate and increased carbon dioxide gas flow rate.

The numeral 2' denotes overflow ribs formed integrally with the end portion of the member 2 and arranged at a predetermined distance from the oxygen inlet 9 so that the oxygen gas blown into the interior of the mounting cover may be diffused by impinging on the ribs 2'. The oxygen gas blown through inlet 9 is diffused in this manner and directed to an outlet 10 with an unlocalized flow pattern in order to prevent the nonuniform distribution of the gas exchange ratio resulting from a channeling phenomenon.

The packing ratio of the hollow fibers 5 at the constricted portion 16 is preferably 60 to 80 percent, for the following reason. With a packing ratio lower than about 60 percent, certain fibers may not be constricted by the constrictor portion 14, resulting in an uneven distribution of the fibers 5 and channeling, thus lowering the efficiency. Moreover, the fiber bundle 15 cannot be easily positioned centrally of the tubular section, thus giving rise to difficulties from the viewpoint of manufacture. With the packing ratio higher than about 80 percent, the hollow fibers 5 abutting against the constrictor 14 may be crushed under a strong pressure to obstruct the blood flow and hence, lower the efficiency and cause blood to remain in the fibers. In addition, difficulties may be caused in point of manufacture because of excessively tight binding of the hollow fiber bundle 15.

The packing ratio in the tubular main member 2 is selected to be about 30 to 60 percent for the following reason. With a ratio lower than about 30 percent, the hollow fibers 5 may become offset within the tubular main member 2 to lower the exchange efficiency and give rise to difficulties in point of manufacture. With a ratio higher than about 60 percent, the hollow fibers 5 may become compacted and stick to one another, resulting in a lower efficiency.

The packing ratio at the outer surfaces of the walls 6, 7 is selected to be approximately 20 to 40 percent for the following reason. With a ratio of less than about 20 percent, the distribution of the open ends of the hollow fibers 5 may be uneven due to difficulties in manufacture, resulting in a nonuniform blood flow pattern and the problem of thrombus. On the other hand, with ratio above 40 percent, the fibers 5 tend to be compacted from place to place, resulting in local vacancies of the potting agent that makes up the walls 6, 7, thus causing leakage.

In the above embodiment, the constrictor 14 projected from the inner wall of the housing 1 is cast or formed integrally with the housing 1. The present invention is not limited to this mode of execution.

Thus, a separate annular member may be used or an annular recess may be provided on the central portion of the tubular main member. Alternatively, the inner wall of the main member may be tapered so that the inside diameter will be smallest at the center and become progressively larger towards both ends.

The heat exchanger section B has a housing 21 of the same configuration as the housing 1 of the oxygenator section A and the housing 21 is formed by a tubular main member 22, externally threaded mounting covers 23, 24 respectively provided with an outlet 30 and an inlet 29 for a heat exchange medium, and a blood port 31 having a blood outlet 33.

Figure 2:
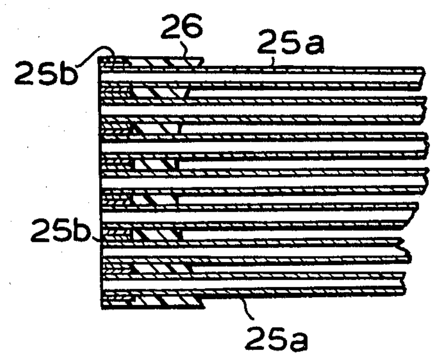
FIG. 2 is a sectional view of the end portion of the heat exchanger section shown in FIG. 1.

Numeral 22' denotes overflow ribs provided on the end of the tubular main member 22 and adapted to diffuse the heat exchange medium supplied from inlet 29 prior to introduction into heat exchange medium chamber 28 and to deliver the heat exchange medium with an unlocalized flow pattern to the outlet 30. In the housing 21, a multiplicity of tubes 25 are arranged parallel to the longitudinal direction of the housing 21, these tubes 25 being separated physically from one another and supported at both ends by walls 26, 27 within mounting covers 23, 24, the walls being made of the cast and hardened potting material as are the walls 6, 7 of the section A. A heat exchange medium chamber 28 is delimited by the walls 26, 27, the outer peripheral surfaces of the tubes 25 and the inner surface of the housing 21. As seen in FIG. 2, each tube 25 consists of a small diameter pipe 25*a* and a sleeve 25*b* of synthetic material. The pipe 25*a* has an inside diameter of 1 to 3 mm, a wall thickness of 0.05 to 0.2 mm and a length of 150 to 300 mm, and is made of stainless steel or other metallic material that has good heat resistance and thermal conductivity, and that is inexpensive and not likely to flex even with reduced wall thicknesses. Both ends of each small diameter tube 25*a* are covered with sleeves 25*b* to a length of about 5 mm, the sleeve 25*b* having a wall thickness of 1 mm, an overall length of 20 to 50 mm and an inside diameter slightly smaller than the outside diameter of the small diameter tube 25*a* and being made of hardenable resin such as silicone or polyurethane having a Shore A hardness in the range of 95 to 98.

The sleeves 25*b* may preferably be of such material that has similar physical and chemical properties as those of the pressure resistant walls 26 supporting the tubes 25. For instance, should the pressure-resistant walls 26 be made of polyurethane, then the latter may preferably be used as the material for sleeves 25*b*.

Should the material for the wall 26 and that for sleeves 25*b* not be compatible with each other, as when using polyurethane for wall 26 and polyethylene for sleeves 25*b*, the latter should be subjected to surface treatment in order to furnish such compatibility. Thus the outer wall surfaces of the sleeves 25*b* should be oxidized by treatment with chemicals or flame, or treated by corona or plasma discharge.

The multiple tube-type heat exchanger section described above may be manufactured as follows. A multiplicity of tubes 25, each consisting of a small diameter tube 25*a* and sleeves 25*b* of synthetic material fitted and secured to both ends of the tubes 25*a*, are prepared. The open ends of the small diameter tubes are preferably chamfered. From 10 to 100 tubes of the same size are bundled as one unit so that both tube ends may be aligned. Then, both ends of the tubes are secured by contracting tubes or by winding rubber bands around them.

The distance between the adjacent tubes 25 may be changed freely by using the sleeves 25*b* of various wall thicknesses.

Then, the open ends of each tube 25 are plugged. This plugging operation may be made at any time before fitting into a mold cap 40 to be described later. This operation may be dispensed with, provided that one of the sleeves 25*b* has sealed ends from the outset.

Figure 3:
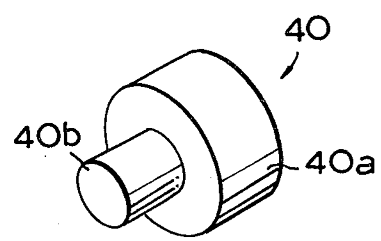
FIG. 3 is a perspective view of a mold cap used for manufacture of the heat exchanger section shown in FIG. 1.

Next, the thus bundled tubes are introduced into the housing 21. The mold cap 40 as shown in FIG. 3 is then prepared. The mold cap is preferably made of a material that can be molded to a predetermined shape and that can be cut off with a knife. The small diameter sleeve portion 40*b* of the mold cap 40 has an inside diameter equal to the outside diameter of the tube bundle, whereas the large diameter sleeve portion 40*a* of the mold cap 40 has an inside diameter equal to the outside diameter of the mounting caps 23, 24 of the housing 21. The tube bundle is inserted into the small diameter portion 40*b* of the mold cap 40 to positively hold the tubes 25, whereas the large diameter portion 40*a* of the mold cap 40 is inserted into the interior of the covers 23, 24.

When pouring the hardenable resin into an outer tube portion by centrifugal injection as discussed below, a compression cap having the same inner contour as the outer contour of the mold cap is preferably fitted to both ends of the outer tube portion on which the mold cap is mounted, to prevent leakage of hardening resin. Then, as the housing 21 is kept revolving about its central longitudinal axis for 15 to 20 minutes, elastomeric material, such as silicon, polyurethane or polyvinyl chloride is injected into the outer tube portion from both end sides by centrifugal injection. The resin thus injected flows towards both ends of the outer tube portion. Pressure-resistant walls 26, 27, fixedly supporting both ends of the tubes 25 at the opening portions of the outer tube portion, may thus be completed upon hardening of the injected resin.

The compression cap is removed from both ends of the outer tube portion, and the mold cap as well as the pressure resistant walls fixedly supporting the tubes 25 are cut off in a direction perpendicular to the axial direction of the outer tube portion to expose the ends of the tubes 25.

In a case where the small diameter pipes 25*a* fixedly supported by walls 26, 27 are made of metal, the plastic tube portions may be cut off at the sleeves 25*b* without cutting the metal, thereby avoiding the formation of burrs.

Next, blood port 31 is connected to the mounting cover 23 of housing 21 with a threaded ring 42.

The inner surface of the mold cap 40 is preferably coated in advance with material that is not adhesive to the hardening resin. In this case, the mold cap 40 may be detached easily from the walls 26, 27, so that the mold cap need not be cut off while still attached. For instance, when polyurethane is used as the hardening resin, the inner surface of the mold cap may be coated with fluorine resin.

In the oxygenator section A and the heat exchanger section B having the above construction, the confronting mounting covers 4, 24 are formed with threaded portions advancing in opposite directions, as shown in FIG. 1. These mounting covers 4, 24 are connected together from outside by a threaded connector ring 36 for delimiting a blood chamber 38 therebetween by the medium of a support member 37 having O-rings 34, 35 as shown.

Figure 4:
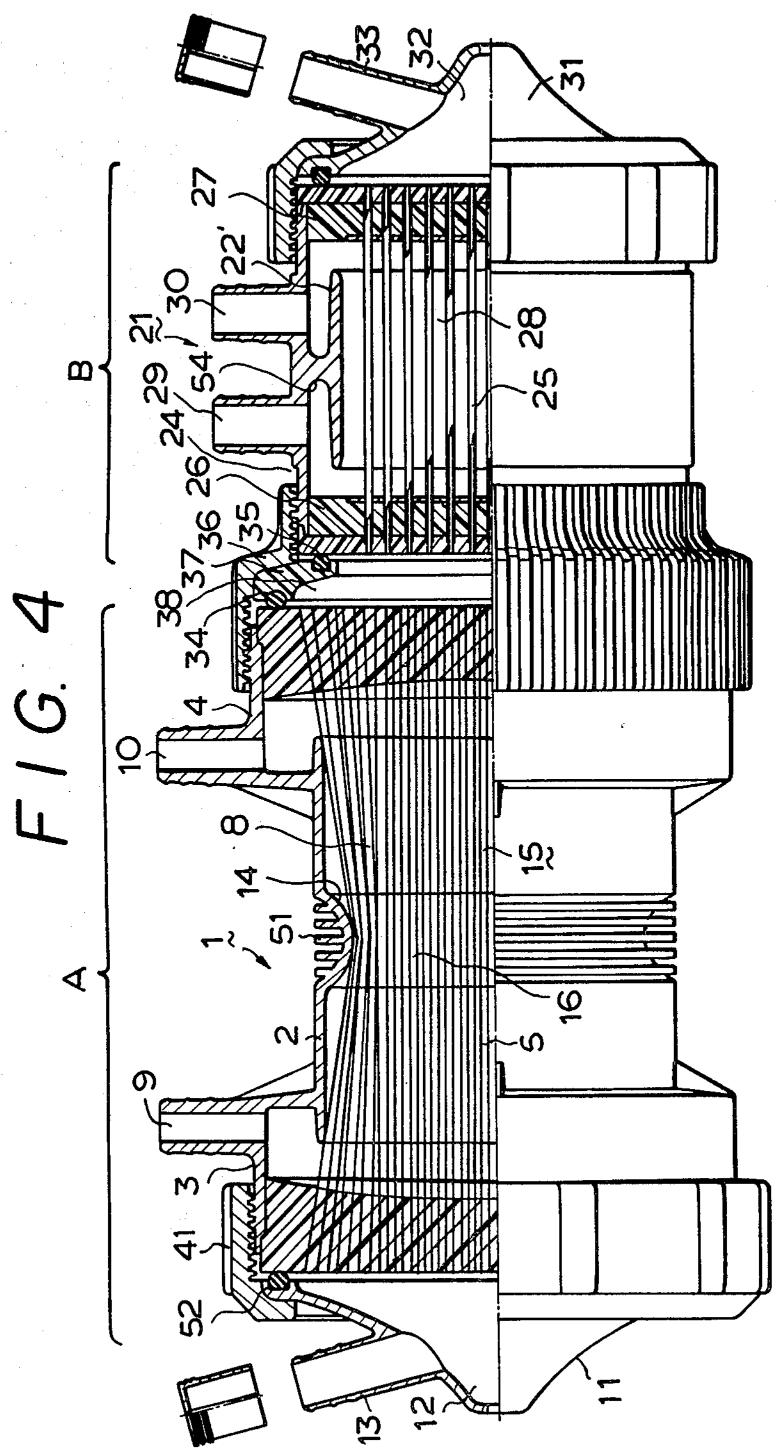
FIG. 4 is a partially sectional view of a hollow fiber type artificial lung having an enclosed heat exchanger according to a modified embodiment.

FIG. 4 shows in cross-section a hollow fiber-type artificial lung with an enclosed heat exchanger according to a modified embodiment of the present invention. Since the construction and operation of this modified embodiment are essentially the same as those of the device shown in FIG. 1, only the portion different from the device of FIG. 1 will be explained below and any overlapping description will be omitted for brevity. The parts of the device of FIG. 4 that are the same as those of the preceding embodiment are indicated by the same reference numerals used in FIG. 1.

The blood supplied to a blood port 11 by way of an inclined inlet 13 reaches a blood chamber 38 by way of the constricted portion 16 provided by the constrictor 14 of the tubular main member 2. Numeral 51 denotes fins for reinforcing the constrictor portion 14, and numeral 52 denotes O-rings for assuring a liquid-tight connection between the port 11 and the housing 1 that is effected by means of a threaded ring 41. The oxygenator section A and the heat exchanger section B are connected together with a blood chamber 38 therebetween by means of a connector ring 36 connecting the mounting covers 4, 24 to each other. This construction permits the number of tubes 25 of the heat exchanger section to be changed as desired. The speed of the blood flow through the tubes 25 is determined by the number of tubes 25 if the diameters of the tubes 25 are the same. Thus, the blood flow per unit time may be selected as desired by suitably selecting the number of tubes 25. For instance, if the blood should be warmed for surgical purposes or as required for certain patients, the number of tubes 25 may be increased to adjust the blood flow per unit time to a smaller value. By designing an oxygenator section A and a heat exchanger section B during the manufacturing stage so as to have several varieties of oxygenating capability and several varieties of heat exchange capability, respectively, the hollow fiber-type artificial lung having an enclosed heat exchanger may be adapted to a variety of practical use situations by judicious selection of these capabilities.

Numeral 22' denotes overflow ribs having a common wall 54 dividing an inlet 29 and an outlet 30 for the heat exchange medium. The heat medium introduced through inlet 29 is distributed over the tubes by overflow ribs 22' and delivered to the outlet 30 with a non-localized flow pattern. By having the blood outlet 33 oriented at the same angle with or in symmetry with the blood inlet 13, the blood conduits to be connected to the inlet and outlet may be oriented in the desired direction. This arrangement is convenient for manipulation and helps to reduce the size of the overall device.

The measurements of the oxygenator section A and the heat exchanger section B and the numbers of the hollow fibers 5 and tubes 25 may be given as follows.

The length of the oxygenator section A is about 150 to 170 mm, and it has an outside diameter of about 50 to 150 mm. About 10,000 to 60,000 hollow fibers are arranged therein. The heat exchanger section B has a diameter of about 80 to 110 mm. 50 to 600 tubes are arranged in the section B and they have an effective range of operation of about 60 to 80 mm. The entire length of the hollow fiber-type artificial lung having an enclosed heat exchanger according to the preferred embodiment is about 330 to 420 mm.

OPERATION OF THE INVENTION

The hollow fiber-type artificial lung having an enclosed heat exchanger according to the present invention may be installed in an extra-corporeal blood circulating circuit and perform the same function as the separately installed heat exchanger and oxygenator of the prior art. The blood may be introduced by a blood pump, not shown, by way of a blood inlet 13, then passed through a blood chamber 12 and then passed through respective hollow fibers 5. During this interval, the blood is oxygenated with oxygen introduced from the oxygen inlet into oxygen chamber 8, and carbon dioxide gas is discharged. Oxygen contained in oxygen chamber 8 is discharged by way of outlet 10 together with carbon dioxide gas.

Upon arriving at blood chamber 38, the blood is passed through each tube 25 and warmed or cooled with the heat exchange medium, such as warm water or cool water, introduced into heat exchange medium chamber 28 by way of inlet 29. The warmed or cooled blood is then delivered to a blood efflux chamber 32 and returned to the patient's body by way of blood outlet 33 and the blood circulating circuit. The medium contained in chamber 28 is discharged through outlet 30.

The blood flow can be reversed if the situation so demands. In this case, the blood is first warmed or cooled in heat exchanger B and then oxygenated in oxygenator A where carbon dioxide gas is further discharged and the blood is returned to the patient's body.

EFFECT OF THE INVENTION

As discussed above, this invention resides in a hollow fiber type oxygenator section having an enclosed heat exchanger section, and the circuit tubing to be used for connecting these sections may be omitted with subsequent reduction in priming. Moreover, the defoaming operation need not be effected first in the oxygenator and then in the heat exchanger or vice versa but only once in the course of priming. Thus, the labor required for defoaming and construction of the blood circuit may be reduced and there can be no error in connection of the oxygenator and heat exchanger.

As many apparently widely different embodiments of this invention may be made without departing from the spirit and scope thereof, it is to be understood that the invention is not limited to the specific embodiments thereof except as defined in the appended claims.

What is claimed is:

1. A hollow fiber-type artificial lung having an enclosed heat exchanger comprising:

(a) an oxygenator section, said oxygenator section including: a first housing; a bundle of a multiplicity of hollow fibers for gas exchange, said hollow fibers having mean pore sizes of 200 to 2,000 angstroms and being gas permeable and liquid impermeable, said hollow fibers being physically separated from one another and arranged side by side within and along the longitudinal direction of said first housing; first and second walls liquid-tightly carrying said hollow fibers at the end portions of said hollow fibers with said end portions of said hollow fibers left open, said first and second walls defining an oxygen chamber with the inner wall of said first housing and outer wall surfaces of said hollow fibers; oxygen inlet and outlet means communicating with said oxygen chamber; and a first blood circulation opening communicating with an interstitial space of said hollow fibers externally of said first wall;

(b) a multiple tube-type heat exchanger section, said heat exchanger section including: a second housing; a multiplicity of tubes physically separated from one another and arranged side by side within and along the longitudinal direction of said second housing; third and fourth walls liquid-tightly carrying said tubes at the end portions of said tubes, with said end portions of said tubes left open, said third and fourth walls defining at heat exchange medium chamber with the inner wall of said second housing and the outer wall surfaces of said tubes; heat exchange medium inlet and outlet means communicating with said heat exchange medium chamber; and a second blood circulation opening communicating with an interstitial space of said tubes externally of said fourth wall; and (c) a blood chamber defining means defining a blood chamber and coupling said oxygenator section directly to said heat exchanger section in substantially coaxial relation and with said open ends of said hollow fibers in face-to-face relation with said open ends of said heat exchanger tubes, said blood chamber being interposed between said second wall of said oxygenator section and said third wall of said heat exchanger section and said second and third walls defining end walls of said blood chamber, said blood chamber communicating said oxygenator and heat exchanger by facing end openings in said hollow fibers carried by said second wall and end openings in said tubes carried by said third wall, and said blood chamber serving as a blood flow buffer chamber so that the processing capability of said oxygenator section and that of said heat exchanger section may be determined independently of each other.

2. The hollow fiber-type artificial lung having an enclosed heat exchanger as claimed in claim 1, in which said first and second housings each have connection terminuses of the same diameter, said connection terminuses having external threads advancing in mutually opposite directions, and said blood chamber defining means includes a threaded connector ring, said first and second housings being connected by said threaded connector ring externally of said connection terminuses with a sealing member interposed between said terminuses.

3. The hollow fiber-type artificial lung having an enclosed heat exchanger as claimed in claim 1, in which said first and second housings have connection terminuses of different diameters, said connection terminuses having external threads advancing in mutually opposite directions, and said blood chamber defining means includes a threaded connector ring, said first and second housings being connected by said threaded connector ring externally of said connection terminuses with a sealing member interposed between said terminuses.

4. The hollow fiber-type artificial lung having an enclosed heat exchanger as claimed in any one of claims 1, 2 or 3, in which the inner wall of said first housing comprises a constrictor for constricting the hollow fiber bundle at a substantially mid portion longitudinally of said hollow fiber bundle.

5. The hollow fiber-type artificial lung having an enclosed heat exchanger as claimed in any one of claims 1, 2 or 3, wherein said hollow fibers of said oxygenator section are provided in a number of from between 10,000 and 60,000.

6. The housing fiber-type artificial lung having an enclosed heat exchanger as claimed in any one of claims 1, 2 or 3, in which said hollow fibers have an inside diameter of about 100 to 1000 $\mu$m, a wall thickness of about 10 to 50 $\mu$m and a porosity of about 20 to 80 percent.

7. The hollow fiber-type artificial lung having an enclosed heat exchanger as claimed in any one of claims 1, 2 or 3, in which said hollow fibers are made of polyolefins.

8. The housing fiber-type artificial lung having an enclosed heat exchanger as claimed in claim 7, in which said hollow fibers have an inside diameter of about 100 and 1000 $\mu$m, a wall thickness of about 10 to 50 $\mu$m and a porosity of about 20 to 80 percent.

9. The hollow fiber-type artificial lung having an enclosed heat exchanger as claimed in claim 8, wherein said hollow fibers of said oxygenator section are provided in a number of from between 10,000 and 60,000.

* * * * *